US012558674B2

(12) United States Patent
Karpov et al.

(10) Patent No.: US 12,558,674 B2
(45) Date of Patent: Feb. 24, 2026

(54) PROCESS FOR PRODUCING A SILVER-BASED EPOXIDATION CATALYST

(71) Applicant: BASF SE, Ludwigshafen am Rhein (DE)

(72) Inventors: Andrey Karpov, Ludwigshafen am Rhein (DE); Christian Walsdorff, Ludwigshafen am Rhein (DE); Thorsten Johann, Ludwigshafen am Rhein (DE); Christian Almer, Ludwigshafen am Rhein (DE); Daniela Rieck, Ludwigshafen am Rhein (DE); Christian Bartosch, Ludwigshafen am Rhein (DE); Mauricio Grobys, Shanghai (CN); Tobias Weinland, Ludwigshafen am Rhein (DE); Holger Borchert, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 719 days.

(21) Appl. No.: 17/914,395

(22) PCT Filed: Mar. 26, 2021

(86) PCT No.: PCT/EP2021/057894
§ 371 (c)(1),
(2) Date: Sep. 26, 2022

(87) PCT Pub. No.: WO2021/191414
PCT Pub. Date: Sep. 30, 2021

(65) Prior Publication Data
US 2023/0114770 A1    Apr. 13, 2023

(30) Foreign Application Priority Data
Mar. 27, 2020    (EP) ..................................... 20166189

(51) Int. Cl.
*B01J 23/68* (2006.01)
*B01J 37/02* (2006.01)
*B01J 37/14* (2006.01)
*B01J 37/16* (2006.01)
*C07D 301/10* (2006.01)

(52) U.S. Cl.
CPC ......... *B01J 23/688* (2013.01); *B01J 37/0203* (2013.01); *B01J 37/0205* (2013.01); *B01J 37/14* (2013.01); *B01J 37/16* (2013.01); *C07D 301/10* (2013.01)

(58) Field of Classification Search
CPC ...................................................... B01J 23/688
USPC ......................................................... 549/534
See application file for complete search history.

(56) References Cited

U.S. PATENT DOCUMENTS

| | | | |
|---|---|---|---|
| 5,504,052 | A | 4/1996 | Rizkalla et al. |
| 5,703,253 | A | 12/1997 | Evans et al. |
| 6,452,027 | B1 | 9/2002 | Billig et al. |
| 10,159,961 | B2 | 12/2018 | Natal et al. |
| 2012/0041217 | A1 | 2/2012 | Bhise et al. |

FOREIGN PATENT DOCUMENTS

| | | |
|---|---|---|
| DE | 2300512 A1 | 7/1973 |
| DE | 2454972 A1 | 6/1975 |
| DE | 2521906 A1 | 12/1975 |
| EP | 0014457 A2 | 8/1980 |

(Continued)

OTHER PUBLICATIONS

International Search Report and Written Opinion received for PCT Patent Application No. PCT/EP2021/057894, mailed on Jul. 5, 2021, 8 pages.

*Primary Examiner* — Taofiq A Solola
(74) *Attorney, Agent, or Firm* — Faegre Drinker Biddle & Reath LLP

(57) ABSTRACT

A process for producing a silver-based epoxidation catalyst, comprising i) impregnating a particulate porous refractory support with a first aqueous silver impregnation solution comprising silver ions and an aminic complexing agent selected from amines, alkanolamines and amino acids; ii) converting at least part of the silver ions impregnated on the refractory support to metallic silver by heating while directing a stream of a first gas over the impregnated refractory support to obtain an intermediate catalyst, wherein the first gas comprises at least 5 vol.-% oxygen; iii) impregnating the intermediate catalyst with a second aqueous silver impregnation solution comprising silver ions, an aminic complexing agent selected from amines, alkanolamines and amino acids, and one or more transition metal promoters, in particular rhenium; and iv) converting at least part of the silver ions impregnated on the intermediate catalyst to metallic silver by heating while directing a stream of a second gas over the impregnated intermediate catalyst to obtain the epoxidation catalyst, wherein the second gas comprises at most 2.0 vol.-% oxygen, wherein the impregnated refractory support and the impregnated intermediate catalyst are each heated to a temperature of 200 to 800° C. The process of the invention surprisingly allows for obtaining a catalyst with high selectivity in a cost-efficient manner. The invention also relates to a silver-based epoxidation catalyst obtainable by such a process, and to a process for producing an alkylene oxide by gas-phase oxidation of an alkylene, comprising reacting an alkylene and oxygen in the presence of a silver-based epoxidation catalyst obtainable by the above process.

17 Claims, No Drawings

(56)            References Cited

FOREIGN PATENT DOCUMENTS

| EP | 0082609 | A1 | 6/1983 |
|----|---------|-----|---------|
| EP | 0085237 | A1 | 8/1983 |
| EP | 0172565 | A2 | 2/1986 |
| EP | 0266015 | A1 | 5/1988 |
| EP | 0339748 | A2 | 11/1989 |
| EP | 0357293 | A1 | 3/1990 |
| WO | 2006/102189 | A1 | 9/2006 |

PROCESS FOR PRODUCING A SILVER-BASED EPOXIDATION CATALYST

CROSS-REFERENCE TO RELATED APPLICATIONS

This application is a national stage application (under 35 U.S.C. § 371) of PCT/EP2021/057894, filed Mar. 26, 2021, which claims benefit of European Application No. 20166189.9, filed Mar. 27, 2020, both of which are incorporated herein by reference in their entirety.

The present invention relates to a process for producing a silver-based epoxidation catalyst, i.e. a catalyst effective in the oxidative conversion of an alkylene to an alkylene oxide, the silver-based epoxidation catalyst obtainable by this process, and a process for producing an alkylene oxide by gas-phase oxidation of an alkylene by means of oxygen in the presence of the silver-based epoxidation catalyst.

Alkylene oxides, in particular ethylene oxide, are produced in large volume and are primarily used as intermediates in the production of several industrial chemicals. In the industrial oxidation of ethylene to ethylene oxide, e.g., heterogeneous catalysts comprising silver are used. To carry out the heterogeneously catalyzed gas-phase oxidation, a mixture of ethylene and an oxygen-comprising gas, such as air or pure oxygen, is generally passed through a plurality of tubes with a packing of shaped catalyst bodies, wherein the plurality of tubes is located in a reactor.

Catalyst performance is characterized by selectivity, activity, longevity of catalyst activity, and mechanical stability. Selectivity is the molar fraction of the converted alkylene yielding the desired alkylene oxide. Even small improvements in selectivity and the maintenance of selectivity over longer time yield huge dividends in terms of process efficiency.

Epoxidation catalysts typically contain high levels of silver, e.g., at least 15 wt.-% of silver. Silver-containing catalysts may be prepared by impregnating a refractory support with an impregnation solution and calcining the impregnated support at high temperatures so as to obtain the silver-containing catalyst. Calcination of the impregnated support is typically performed under an inert gas atmosphere, such as a nitrogen atmosphere.

U.S. Pat. No. 5,504,052 describes a silver-based catalyst for ethylene oxidation, wherein the catalyst is prepared by impregnating an inert support with a silver/amine solution and calcining the impregnated support at 300 to 500° C. for a time sufficient to reduce the silver component to metallic silver and to remove volatile decomposition products from the silver containing support. U.S. Pat. No. 5,504,052 deems it critical that contact of the silver-containing support with an oxygen-containing atmosphere is avoided at least at temperatures above about 250° C., as it is believed that at temperatures of 250° C. and higher oxygen is absorbed in substantial quantities into the bulk of the silver, where it has an adverse effect on the catalyst characteristics.

This process uses great quantities of inert gas, and can be expensive. US 2012/0041217 A1 describes a process for producing a silver-based ethylene oxide catalyst, wherein an impregnated support is subjected to a first calcination in a first atmosphere comprising air, and subsequently subjected to a second calcination in a second atmosphere comprised of an inert gas.

It is an object of the present invention to provide an efficient process for producing silver-based epoxidation catalysts with reduced overall process costs, without compromising the performance of the catalysts thus produced. The invention further seeks to provide catalysts with still improved selectivity.

The invention relates to a process for producing a silver-based epoxidation catalyst, comprising i) impregnating a particulate porous refractory support with a first aqueous silver impregnation solution comprising silver ions and an aminic complexing agent selected from amines, alkanolamines and amino acids;

ii) converting at least part of the silver ions impregnated on the refractory support to metallic silver by heating while directing a stream of a first gas over the impregnated refractory support to obtain an intermediate catalyst, wherein the first gas comprises at least 5 vol.-% oxygen;

iii) impregnating the intermediate catalyst with a second aqueous silver impregnation solution comprising silver ions, an aminic complexing agent selected from amines, alkanolamines and amino acids, and one or more transition metal promoters, in particular rhenium; and iv) converting at least part of the silver ions impregnated on the intermediate catalyst to metallic silver by heating while directing a stream of a second gas over the impregnated intermediate catalyst to obtain the epoxidation catalyst, wherein the second gas comprises at most 2.0 vol.-% oxygen;

wherein the impregnated refractory support and the impregnated intermediate catalyst are each heated to a temperature of 200 to 800° C.

It was found that the process of the invention surprisingly allows for obtaining a catalyst with high selectivity. In particular, it was found that the selectivity of a catalyst obtained by the process of the invention is as high as for a catalyst obtained by a comparable process wherein both of the two heating steps are conducted in the presence of an inert gas. Conversely, the presence of an oxygen-containing gas in both of the two heating steps, or in the second of the two heating steps, has been found to be detrimental to the selectivity of the thus-obtained catalysts. Performing heating step ii) in the presence of an oxygen-containing gas instead of an inert gas allows for a simplified and cost-efficient production process.

In step i) of the process, the particulate porous refractory support is impregnated with a first aqueous silver impregnation solution comprising silver ions and an aminic complexing agent selected from amines, alkanolamines and amino acids. In step iii) of the process, the intermediate catalyst obtained in step ii) is impregnated with a second aqueous silver impregnation solution comprising silver ions, an aminic complexing agent selected from amines, alkanolamines and amino acids, and one or more transition metal promoters, in particular rhenium.

Suitably, the silver ions are silver cations, in particular silver cations with an oxidation state of +1, i.e. $Ag^{+1}$ or $Ag^+$.

The first aqueous silver impregnation solution and/or the second aqueous silver impregnation solution may comprise a carboxylate anion. Without wishing to be bound by theory, it is believed that carboxylate anions are capable of serving as reducing agents for silver cations, promoting the conversion of silver anions to metallic silver. Preferably, the first aqueous silver impregnation solution and the second aqueous silver impregnation solution each comprise a carboxylate anion.

Preferably, the first aqueous silver impregnation solution and the second aqueous silver impregnation solution comprise a carboxylate anion selected from the group consisting of oxalate, citrate, phthalate, lactate, propionate, butyrate, malonate and higher fatty acid anions and combinations thereof. Most preferably, the first aqueous silver impregnation solution and the second aqueous silver impregnation solution each comprise oxalate.

In a preferred embodiment, the silver ion and the carboxylate anion are comprised as a silver carboxylate, such as silver oxalate, silver citrate, silver phthalate, silver lactate, silver propionate, silver butyrate, silver malonate and higher fatty acid salts and combinations thereof. Silver oxalate is especially preferred.

Favorably, silver carboxylates can decompose at relatively mild temperatures, with the silver cations being converted to metallic silver and the carboxylate anions being converted to easily removable components, such as carbon dioxide. For example, silver oxalate decomposes to metallic silver and carbon dioxide at approximately 150° C.

The above silver salts may be generated, e.g., by reaction of a silver compound and an acid. For example, silver oxalate may be obtained from the reaction of silver (I) oxide, i.e. $Ag_2O$, and oxalic acid in an aqueous solution, preferably in the presence of the complexing agent such as an aminic complexing agent like a $C_1$-$C_{10}$-alkylenediamine. In the presence of ethylenediamine and water, e.g., a soluble silver complex is formed. Preferably, the molar ratio of oxalic acid to silver is in the range from 0.4 to 0.65, more preferably 0.5 to 0.6, in particular 0.505 to 0.6. It has been found that the amount of undissolved solids is minimized when the oxalic acid is used in a slight stoichiometric excess over the silver ions.

The first aqueous silver impregnation solution and the second aqueous silver impregnation solutions each comprise an aminic complexing agent selected from amines, alkanolamines and amino acids. The aminic complexing agent can be any amine, alkanolamine or amino acid known in the art to function as a complexing and/or solubilizing agent for silver cations. Generally, the aminic complexing agent possesses at least one primary or secondary amino group. The aminic complexing agent is suitably completely soluble in water, or water in admixture with a water-soluble solvent.

The aminic complexing agent may comprise an amine selected from the group consisting of alkylamines, alkylenediamines, dialkylenetriamines, and mixtures thereof. The aminic complexing agent may in particular comprise an amine selected from the group consisting of $C_1$-$C_{10}$-alkylamines, $C_1$-$C_{10}$-alkylenediamines, and $C_1$-$C_{12}$-dialkylenetriamines.

Suitable alkylamines include ethylamine, diethylamine, n-propylamine, di(n-propylamine), isopropylamine, diisopropylamine, n-butylamine, isobutylamine, sec-butylamine, and t-butylamine. Suitable alkylenediamines include vicinal $C_2$-$C_6$-alkylenediamines, such as ethylenediamine (EDA) and 1,2-propylenediamine. Further suitable alkylenediamines include 1,3-propylenediamine and 1,4-butylenediamine. Suitable dialkylenetriamines include diethylenetriamine and dipropylenetriamine.

Preferably, the aminic complexing agent comprises an amine selected from alkylenediamines, more preferably $C_1$-$C_{10}$-alkylenediamines, even more preferably vicinal $C_2$-$C_6$-alkylenediamines. In particular, the aminic complexing agent comprises ethylenediamine.

In another embodiment, the aminic complexing agent may comprise an alkanolamine, such as a $C_1$-$C_{12}$-alkanolamine, or a mixture of $C_1$-$C_{12}$-alkanolamines. Suitable alkanolamines include ethanolamine, diethanolamine, triethanolamine, propanolamine (i.e., 1-amino-2-propanol or 1-amino-3-propanol), and dipropanolamine (i.e., bis(3-hydroxypropyl)amine).

In another embodiment, the aminic complexing agent may comprise an amino acid. The amino acid can be any of the known natural or unnatural amino acids, in particular any of the known essential amino acids. The amino acid typically has an underivatized amino end group, i.e. —$NH_2$ or —$NH_3^+$, and an underivatized carboxylic end group, i.e. —COOH or —$COO^-$. In the event of a charge on any or both of the amino and carboxyl end groups, the amino acid is understood to possess a suitable counterion.

Suitable amino acids include glycine, alanine, valine, leucine, isoleucine, cysteine, methionine, phenylalanine, tyrosine, tryptophan, proline, serine, threonine, asparagine, glutamine, aspartic acid, glutamic acid, histidine, lysine, and arginine. Generally, the amino acid is an alpha-amino acid. However, beta-amino acids, e.g., beta-alanine and beta-aminobutyric acid, and gamma-amino acids, e.g., gamma-aminobutyric acid, are also suitable.

Preferably, the amino acid is selected from glycine, alanine, valine, leucine, isoleucine, and mixtures thereof, more preferably from glycine, alanine, valine, and mixtures thereof, even more preferably from glycine, alanine, and mixtures thereof, and is most preferably glycine.

Preferably, the aminic complexing agent evaporates and/or decomposes in the heating steps ii) and iv) of the present process.

The relative amounts of water, silver ions and aminic complexing agent in the first aqueous silver impregnation solution and in the second aqueous silver impregnation solution are not especially limited. Preferably, the molar ratio of amine nitrogen atoms of the aminic complexing agent to silver ions is at least 2.66, e.g., at least 2.76, preferably at least 2.86, most preferably at least 3.00. When the aminic complexing agent is an alkylenediamine, such as ethylenediamine, the molar ratio of diamine to silver ions is thus at least 1.33, e.g., at least 1.38, preferably at least 1.43, most preferably at least 1.50.

The amount of aminic complexing agent comprised in the first aqueous silver impregnation solution and in the second silver impregnations solution may be at least 23 wt.-%, in particular at least 24 wt.-%, preferably at least 25 wt.-%, most preferably at least 26 wt.-%, based on the total amount of aminic complexing agent in the respective impregnation solution.

It is generally preferred to use silver impregnation solutions having a high content of dissolved silver ions. Preferably, the first aqueous silver impregnation solution and the second silver impregnation solutions contain 24 to 40 wt.-%, e.g. 25 to 35 wt.-%, in particular 26 to 33 wt.-%, preferably 27 to 32 wt.-%, more preferably 28 to 31 wt.-% and most preferably 29 to 30 wt.-% of dissolved, e.g., complexed, silver ions. The content of dissolved silver ions is calculated based on all silver ions which are homogeneously dissolved in the silver impregnation solution. The homogeneously dissolved silver ions comprise silver ions complexed by an aminic complexing agent and silver ions dissolved in any other form.

The first aqueous silver impregnation solution and/or second aqueous silver impregnation solution may further include at least one silver concentration enhancer, selected from ammonium salts.

In one embodiment, the silver concentration enhancer is at least one ammonium salt having an anionic component that is thermally decomposable. As used herein, the term "thermally decomposable" indicates that the anion decomposes, generally to gaseous species, which temporarily leaves the ammonium ion isolated. Without wishing to be bound by theory, it is believed that the isolated ammonium ion reacts with the aminic complexing agent to form ammonia, which complexes silver ions to form a silver complex of high solubility.

Examples of suitable ammonium salts include ammonium carboxylates, ammonium carbonate, ammonium bicarbonate, ammonium nitrate, ammonium phosphate, diammonium hydrogen phosphate, and ammonium dihydrogen phosphate.

Examples of suitable ammonium carboxylates include ammonium formate, ammonium acetate, ammonium propionate, ammonium butyrate, ammonium valerate, ammonium oxalate, ammonium hydrogen oxalate, ammonium malonate, ammonium hydrogen malonate, ammonium succinate, ammonium hydrogen succinate, ammonium maleate, ammonium hydrogen maleate, ammonium fumarate, ammonium hydrogen fumarate, ammonium malate, ammonium hydrogen malate, ammonium citrate, ammonium tartrate, ammonium lactate, ammonium aspartate, and ammonium glutamate.

The silver concentration enhancer may be present in the silver impregnation solution in an amount of at least 1 wt.-%, relative to the total weight of the impregnating solution, such as at least 5 wt.-% or at least 10 wt.-%, and is typically comprised in amounts of less than 60 wt.-%, relative to the total weight of the impregnating solution, preferably less than 45 wt.-%, more preferably less than 30 wt.-%.

The first aqueous silver impregnation solution and/or the second aqueous silver impregnation solution may also include a non-aminic oxygenated compound selected from polyols, hydroxycarboxylic acids, or mixtures thereof. In a preferred embodiment, the non-aminic oxygenated compound comprises two to four carbon atoms.

The non-aminic oxygenated compound is favorably water soluble and completely dissolved in the impregnation solution. The non-aminic oxygenated compound typically has a high boiling point of at least 100° C., such as at least 150° C., at least 250° C. or at least 400° C.

It has been found that the presence of a non-aminic oxygenated compound in the silver impregnating solution results in an ethylene oxidation catalyst having a significantly improved performance in selectivity and/or activity, particularly in the start-up phase of an ethylene oxidation process.

Suitable polyols typically contain two to four carbon atoms and two to four hydroxy groups (OH). Examples of such polyols include ethylene glycol, diethylene glycol, propylene glycol, glycerol, erythritol, and 1,1,2,2-ethanetetrol.

Suitable hydroxycarboxylic acids typically contain two to four carbon atoms and comprise at least one hydroxy group and at least one carboxylic acid group. Examples of such hydroxycarboxylic acids include glycolic acid, 2-hydroxypropionic acid (lactic acid), 3-hydroxypropionic acid, 4-hydroxybutyric acid, and 3-hydroxybutyric acid.

The non-aminic oxygenated compound is typically present in an amount of at least 0.1 wt.-%, relative to the total weight of the silver impregnating solution. The non-aminic oxygenated compound may for example be present in amounts of 0.5 to 5 wt.-%, 1 to 5 wt.-%, 0.5 to 3 wt.-%, or 1 to 3 wt.-%, based on the total weight of the silver impregnating solution.

The first aqueous silver impregnation solution and/or second aqueous silver impregnation solution may also include a surfactant. It has been found that the presence of various surfactants in the silver impregnation solution can improve its drainage from the carrier during the catalyst synthesis. As a result, the amount of silver impregnation solution may be significantly reduced without reducing the catalyst performance.

Additionally, the use of surfactants can provide ethylene oxide catalysts having a reduced external surface agglomeration of silver. Advantageously, this allows for simplified catalyst handling after calcination due to reduced dust and debris formation. This effect may moreover reduce the pressure drop typically observed during ethylene oxide production.

The surfactant for use in the present invention can be any material capable of reducing the surface tension between the silver impregnation solution and the carrier surface, which does not unduly interfere with subsequent catalyst manufacturing processing steps or final catalyst performance. Examples of surfactants include nonylphenol ethoxylates, alkyl polyglucosides, phosphate esters, secondary alcohol alkoxylates, alkylphenyloxide disulfonate salts, low foam surfactants, sulfates and sulfonates. Commercially available compounds which may be useful in the present invention include: TERGITOL™ 15S9, TERGITOL™ NP-9, TRITON™ CF-10, TRITON™ CF-32, TRITON™ CF-76 and ECOSURF™ LF 30 (all from the Dow Chemical Company); DYNOL™ 604, and Surfynol® 440 (both from Evonik Industries); and ENVIROGEM® AD01 (from Air Products). Two or more surfactants may be used together.

Typically, the surfactant should be added in an amount of from 0.05 wt.-% of the solution, preferably 0.1 wt.-% up to 2 wt.-%, more preferably 1 wt.-%. The desired amount of surfactant may depend on the concentration of silver (or other nanoparticles) in the solution. For silver-containing solutions, it is suggested that the surfactant be added in an amount of 0.1 wt.-% to 8 wt.-% preferably about 2 wt.-% to 6 wt.-% of surfactant per unit silver used (for example, if the solution contains 26 wt.-% silver, then the amount of surfactant may be about 4 wt.-%).

It is believed that amounts of surfactants lower than these suggested amounts will still improve the removal of undesired impregnation solution relative to using no surfactant, but the improvement will be less. An amount of surfactant larger than these suggested amounts is also expected to improve the removal of undesired impregnation solution, but with increasing amount of surfactant, its relative effectiveness is expected to decrease. It is also expected that the ranges of most effective surfactant percentage will differ for different surfactants, combinations of surfactants used, or impregnation solution compositions.

In one embodiment, the porous refractory support and the intermediate catalyst are each impregnated at a temperature of 20 to 180° C., preferably 40 to 150° C., more preferably 45 to 100° C., even more preferably 45 to 75° C. and in particular 50 to 60° C. Preferably, impregnation is conducted at a pressure of less than 250 mbar, more preferably at a pressure of less than 100 mbar.

Preferably, the process comprises agitation of the refractory support and the intermediate catalyst during steps i) and iii), respectively. The term "agitation" is understood to refer to a mechanical movement, e.g., shaking, vibrating or tumbling the refractory support or intermediate catalyst. Agitation allows for a more homogenous distribution of impregnation solution on the refractory support and the intermediate catalyst, respectively.

Any impregnation apparatus suitable for impregnation under reduced pressure may be used, including double-cone blenders and free-fall mixing reactors such as tumble dryers.

When impregnation steps i) and/or iii) are performed at temperatures above room temperature (i.e., about 20° C.), the obtained impregnated refractory support and impregnated intermediate catalyst, respectively, may be allowed to cool to room temperature (i.e., about 20° C.) prior to converting at least part of the silver ions by heating.

According to step ii) of the process, at least part of the silver ions impregnated on the refractory support is converted to metallic silver by heating while directing a stream of the first gas over the impregnated support to obtain an intermediate catalyst. According to step iv) of the process, at least part of the silver ions impregnated on the intermediate catalyst is converted to metallic silver by heating while directing a stream of the second gas over the impregnated intermediate catalyst to obtain the epoxidation catalyst.

The first gas comprises at least 5 vol.-% oxygen, preferably at least 10 vol.-% oxygen, more preferably at least 15 vol.-% oxygen, most preferably about 20 vol.-% oxygen. It is understood that the term "oxygen" refers to molecular oxygen, i.e. $O_2$, in the context of this invention, unless indicated otherwise. For example, the first gas may comprise lean air having an oxygen content of 5 to 20° vol.-%, produced, e.g., by suitable dilution of air with an inert gas such as molecular nitrogen. Most preferably, the first gas is air. The use of air as the first gas allows for an especially cost-efficient process.

The second gas comprises less than 2.0 vol.-% oxygen, preferably less than 1.0 vol.-% oxygen, more preferably less than 0.5 vol.-% oxygen, most preferably less than 0.1 vol.-% oxygen, such as less than 0.05 vol.-% oxygen or less than 0.01 vol.-% oxygen. The second gas preferably comprises an inert gas, such as nitrogen, argon, krypton or helium, in particular nitrogen, for example in a concentration of at least 98 vol.-%, preferably at least 99 vol.-%, more preferably at least 99.5 vol.-%, most preferably at least 99.9 vol.-%, such as at least 99.95 vol.-% or at least 99.99 vol.-%. In one embodiment, the second gas comprises at least 99 vol.-% nitrogen, preferably at least 99.5 vol.-% nitrogen, most preferably at least 99.9 vol.-% nitrogen, such as at least 99.95 vol.-% nitrogen or at least 99.99 vol.-% nitrogen.

In steps ii) and iv), water evaporates and the aminic complexing agent evaporates and/or decomposes from the impregnation solution upon heating, causing a silver compound to precipitate from the solution and be deposited onto the refractory support or the intermediate catalyst, respectively. At least part of the deposited silver compound is subsequently converted to metallic silver upon further heating. Metallic silver is the catalytically active species of the epoxidation catalyst. Preferably, the silver compound is a silver carboxylate, in particular silver oxalate.

The phrase "converting at least part of the silver ions to metallic silver" is understood to mean that a significant amount of the silver ions is converted to metallic silver, in particular at least 70 mol-% of the silver ions, preferably at least 90 mol-%, more preferably at least 95 mol-% and most preferably at least 99.5 mol-% or at least 99.9 mol-%, i.e. essentially all silver ions, based on the total molar amount of silver in the intermediate catalyst and the epoxidation catalyst, respectively. The amount of the silver ions converted to metallic silver can for example be determined via X-ray diffraction (XRD) patterns.

The impregnated refractory support and the impregnated intermediate catalyst are each heated at a temperature of 200 to 800° C., preferably 210 to 650° C., more preferably 220 to 500° C., most preferably 220 to 350° C. Preferably, the heating rate in the temperature range of 40 to 200° C. is at least 20 K/min, more preferably at least 25 K/min, such as at least 30 K/min.

During impregnation, the aqueous silver impregnation solution penetrates into the pores of the support by absorption and/or capillary action. Without wishing to be bound by theory, it is believed that the above-described high heating rates in the temperature range of 40 to 200° C. allow for fast evaporation of water and fast evaporation and/or decomposition of the aminic complexing agent. Advantageously, this allows for a homogenous distribution of silver on the porous support and within its pores. When the heating rate is too low, it is believed that the silver concentration on the support's surface increases.

In a preferred embodiment, the impregnated refractory support and the impregnated intermediate catalyst, respectively, are heated at an absolute pressure in the range of 0.5 bar to 35 bar, in particular in the range of 0.9 to 1.1 bar, such as at atmospheric pressure (approximately 1013 mbar). Typical total heating times range from 5 to 60 min, such as 7 to 30 min. In general, the higher the temperature, the shorter the heating period required for conversion of the silver ions to metallic silver. A continuous or step-wise heating program may be used for this purpose.

In the following, for the sake of conciseness, the impregnated refractory support and the impregnated intermediate catalyst are collectively referred to as impregnated bodies.

Determining the temperature of the heated impregnated bodies directly may pose practical difficulties. Hence, for the purposes of the present application, the temperature of the heated impregnated bodies is considered to be the temperature of the gas immediately after the gas has passed over the impregnated bodies. In a practical embodiment, the impregnated bodies are placed on a suitable surface, such as a wire mesh or perforated calcination belt, and the temperature of the gas is measured by one or more thermocouples positioned adjacent to the opposite side of the impregnated bodies which first comes into contact with the gas. The thermocouples are suitably placed close to the impregnated bodies, e.g., at a distance of 1 to 30 mm, such as 1 to 3 mm or 15 to 20 mm from the impregnated bodies. The use of a plurality of thermocouples can improve the accuracy of the temperature measurement. Where several thermocouples are used, these may be evenly spaced across the area on which the impregnated bodies rest on the wire mesh, or the breadth of the perforated calcination belt. The average value is considered to be the temperature of the gas immediately after the gas has passed over the impregnated bodies. To heat the impregnated bodies to the temperatures as described above, the first gas and second gas typically each have a temperature of 220 to 800° C., more preferably 230 to 550° C., most preferably 240 to 350° C.

The expression "directing a stream of a gas over the impregnated bodies" is intended to mean that the gas stream passes over the surface of the impregnated bodies so as to remove gaseous decomposition products and volatilized compounds. This includes a situation where the gas passes over the surface of an individual impregnated body or situations where the gas passes through an arrangement of impregnated bodies situated beside one another and optionally above one another, such as a bed of impregnated bodies. It is preferable that the bed comprises a low number of layers of impregnated bodies, in particular 1 to 10 layers, preferably 1 to 5 layers, such as 1 to 3 layers. This allows for a favorably fast heating of the individual bodies.

As the gas stream passes over the surface of the impregnated bodies, its composition changes due to the entrainment of gaseous decomposition products and volatilized compounds. In particular, the gas stream may pick up compounds such as water, carbon dioxide, aminic complexing agent and small amounts of ammonia, nitric oxide or ethylene as it passes over the surface of the impregnated bodies. It is understood that the above-defined compositions of the first gas and the second gas relate to the composition of the first gas and the second gas before first reaching the impregnated body or bodies.

In one embodiment, the process of the invention additionally comprises ii') subsequent to ii) and prior to iii), cooling the intermediate catalyst; and/or iv') subsequent to iv), cooling the catalyst.

In step ii'), it is preferred that the intermediate catalyst is cooled to a temperature of 100° C. or lower.

In step iv'), it is preferred that the catalyst is cooled while directing a stream of the second gas over the impregnated intermediate catalyst to obtain the epoxidation catalyst until the temperature of the catalyst is 100° C. or lower. After the catalyst is cooled to this temperature, the catalyst may further be cooled while directing a stream of gas, in particular a stream of the first gas, most preferably air, over the catalyst.

Steps ii) and iv) may be carried out in any type of heating apparatus or furnace, e.g., in a tray furnace or on a belt calciner. Preferably, heating takes place in a step-wise manner. In step-wise heating, the impregnated refractory support or the impregnated intermediate catalyst, respectively, is placed on a moving belt that moves through a furnace with multiple heating zones, e.g., 2 to 8 or 2 to 5 heating zones.

In a preferred embodiment, the impregnated refractory support or the impregnated intermediate catalyst, respectively, enters the furnace at room temperature and is heated to a first temperature of 200° C. to 800° C. in a first zone at a consistently high heating rate. Preferably, the heating rate in the temperature range of 40 to 200° C. is at least 20 K/min, or at least 25 K/min, such as at least 30 K/min. A high heating rate may be achieved by directing a heated gas over the impregnated refractory support or the impregnated intermediate catalyst at a high gas flow.

In subsequent zones, the temperature may be maintained, increased or decreased, typically maintained or decreased under reduced gas flow. If the temperature is not maintained, cooling or heating rates are preferably lower than in the first zone. In the last zone, the catalyst is cooled down to a temperature below 200° C., preferably to ambient temperature, such as 20 to 25° C. Notably, in this last zone a gas may be used which does not fulfill the requirements of the second gas according to step iv). For example, air may be used in the last zone. Different flow rates may be applied to different temperature zones.

The first gas and the second gas are each preferably provided as a gas flow, e.g., a continuous fresh gas flow. A limited amount of a circulating gas flow may be admixed to the fresh gas flow, to the extent that the mixed gas stream fulfills the requirements of the gas compositions of steps ii) and iv). When a circulating gas flow is admixed to the fresh gas flow, at least a part of the circulating gas flow may be purified, e.g., by purging acidic components such as carbon dioxide, or removing water, for example by condensation.

In another embodiment, the first gas and the second gas are each provided as a circulating gas flow. In this case, the circulating gas flow is favorably purified by purging acidic components such as carbon dioxide, or removing water, for example by condensation.

A suitable flow rate for the first gas and/or the second gas may be in the range of, e.g., 1 to 1,000 Nm³/h, 10 to 1,000 Nm³/h, 15 to 500 Nm³/h or 20 to 300 Nm³/h per kg of impregnated bodies. In a continuous process, the term "kg of impregnated bodies" is understood to mean the amount of impregnated bodies (in kg/h) multiplied by the time (in hours) that the stream of the first or second gas, respectively, is directed over the impregnated bodies. It has been found that when the stream of the first or second gas, respectively, is directed over higher amounts of impregnated bodies, e.g., 15 to 150 kg of impregnated bodies, the flow rate may be chosen in the lower part of the above-described ranges, while achieving the desired effect.

The refractory support typically comprises a high proportion of alumina, i.e. $Al_2O_3$, and in particular alpha-alumina, for example at least 50 wt.-%, at least 70 wt.-%, or at least 90 wt.-%, preferably at least 95 wt.-%, most preferably at least 97.5 wt.-%, based on the total weight of the support. Besides alumina, the refractory support may comprise other components, for example binders such as silicates, or other refractory oxides such as zirconia or titania.

The particulate porous refractory support preferably comprises individual shaped bodies. The size and shape of the individual shaped bodies and thus of the catalyst is selected to allow a suitable packing of the shaped bodies in a reactor tube. The shaped bodies suitable for the catalysts of the invention are preferably used in reactor tubes with a length from 6 to 14 m and an inner diameter from 20 mm to 50 mm. In general, the support is comprised of individual bodies having a maximum extension in the range of 3 to 20 mm, such as 4 to 15 mm, in particular 5 to 12 mm. The maximum extension is understood to mean the longest straight line between two points on the outer circumference of the support.

The shape of the support is not especially limited, and may be in any technically feasible form, depending, e.g., on the extrusion process. For example, the support may be a solid extrudate or a hollow extrudate, such as a hollow cylinder. In another embodiment, the support may be characterized by a multilobe structure. A multilobe structure is meant to denote a cylinder structure which has a plurality of void spaces, e.g., grooves or furrows, running in the cylinder periphery along the cylinder height. Generally, the void spaces are arranged essentially equidistantly around the circumference of the cylinder. Preferably, the support is in the shape of a solid extrudate, such as pellets or cylinders, or a hollow extrudate, such as a hollow cylinder. Alternatively, the support may be shaped by tableting.

The porous refractory support typically has a water absorption in the range of 0.35 to 0.70 mL/g (mL of water/gram of support). Preferably, the water absorption of the porous refractory support is in the range of 0.38 to 0.65 mL/g, most preferably 0.41 to 0.60 mL/g. Water absorption refers to vacuum cold water uptake measured at a vacuum of 80 mbar absolute.

Vacuum cold water uptake is determined by placing about 100 g of support ("initial support weight") in a rotating flask, covering the support with deionized water, and rotating the rotary evaporator for 5 min at about 30 rpm. Subsequently, a vacuum of 80 mbar is applied for 3 min, the water and the support are transferred into a glass funnel, and the support is kept in the funnel for about 5 min with occasional shaking in order to ensure that adhering water runs down the funnel. The support is weighed ("final support weight"). The water absorption is calculated by subtracting the initial support weight from the final support weight and then dividing this difference by the initial support weight. It is believed that a water absorption in the above ranges allows for a favorable duration of exposure of the obtained ethylene oxide to the catalyst.

The refractory support generally has a total Hg pore volume in the range of 0.4 to 3.0 mL/g, preferably 0.45 to 1.0 mL/g, or 0.5 to 0.7 mL/g, as determined by mercury porosimetry. Mercury porosimetry may be performed using a Micrometrics AutoPore IV 9500 mercury porosimeter (140 degrees contact angle, 485 dynes/cm Hg surface tension, 60000 psia max head pressure). The Hg porosity is determined according to DIN 66133 herein, unless stated otherwise. It is believed that a Hg pore volume in this range allows for a favorable duration of exposure of the obtained ethylene oxide to the catalyst.

The refractory support generally has a BET surface area of 0.5 to 10 m²/g, preferably 1 to 5 m²/g, or 1.5 to 3 m²/g. The BET method is a standard, well-known method and widely used method in surface science for the measurements of surface areas of solids by physical adsorption of gas molecules. The BET surface is determined according to DIN ISO 9277 herein, unless stated otherwise.

The refractory support may comprise impurities, such as sodium, potassium, iron, silica, magnesium, calcium, zirconium in an amount of 100 to 10000 ppm, based on the total weight of the support.

The refractory support preferably does not have wash-coat particles or a wash-coat layer on its surface, so as to fully maintain the porosity and BET surface area of the uncoated support.

The catalyst obtained by the process preferably comprises at least 15 wt.-% silver, relative to the total weight of the catalyst. Preferably the catalyst has a content of at least 18 wt.-% silver, more preferably at least 20 wt.-% silver, such as 22 wt.-% silver or 25 wt.-% silver, relative to the total weight of catalyst.

For example, the catalyst may comprise 15 to 70 wt.-% silver, relative to the total weight of the catalyst. A preferred catalyst comprises 20 to 60 wt.-% silver, more preferably 20 to 50 wt.-% silver, such as 20 to 40 wt.-% silver, relative to the total weight of the catalyst. A silver content in this range allows for a favorable balance between turnover induced by each catalyst body and cost-efficiency of producing the catalyst.

Thus, the support is preferably impregnated with silver impregnation solution sufficient to obtain a catalyst comprising 15 to 70 wt.-% silver, preferably 20 to 60 wt.-% silver, more preferably 20 to 50 wt.-% silver, such as 20 to 40 wt.-% silver, relative to the total weight of the catalyst.

Preferably, the porous refractory support is impregnated with the first aqueous silver impregnation solution in step i) sufficient so as to obtain an intermediate catalyst in step ii) comprising 5 to 30 wt.-% silver, preferably 10 to 25 wt.-% silver, more preferably 15 to 22 wt.-% silver, relative to the total weight of the catalyst.

Preferably, the intermediate catalyst is impregnated with the second aqueous silver impregnation solution in step iii) sufficient so as to obtain an epoxidation catalyst in step iv) comprising 15 to 50 wt.-% silver, preferably 17 to 40 wt.-% silver, more preferably 20 to 40 wt.-% silver, such as 25 to 40 wt.-% silver, relative to the total weight of the catalyst.

In order to obtain a catalyst with high amounts of silver, steps i) and ii) may be repeated at least once prior to performing steps iii) and iv).

Besides silver, the catalyst may comprise one or more promoting species ("promoter"). A promoting species denotes a component that provides an improvement in one or more of the catalytic properties of the catalyst when compared to a catalyst not containing said component. The promoting species can be any of those species known in the art that function to improve the catalytic properties of the silver catalyst. Examples of catalytic properties include operability (resistance to runaway), selectivity, activity, turnover and catalyst longevity.

The catalyst may comprise a promoting amount of a transition metal or a mixture of two or more transition metals. Suitable transition metals can include, for example, the elements from Groups IIIB (scandium group), IVB (titanium group), VB (vanadium group), VIB (chromium group), VIIB (manganese group), VIIIB (iron, cobalt, nickel groups), IB (copper group), and IIB (zinc group) of the Periodic Table of the Elements, as well as combinations thereof. More typically, the transition metal is an early transition metal, i.e. from Groups IIIB, IVB, VB or VIB, such as hafnium, yttrium, molybdenum, tungsten, rhenium, chromium, titanium, zirconium, vanadium, tantalum, niobium, or a combination thereof. In one embodiment, the transition metal promoter(s) is (are) present in a total amount from 150 ppm to 10000 ppm, typically 225 ppm to 7000 ppm, most typically from 300 ppm to 4000 ppm, expressed in terms of metal(s) relative to the total weight of the catalyst.

Of the transition metal promoters listed, rhenium (Re) is a particularly efficacious promoter for ethylene epoxidation high selectivity catalysts. The rhenium component in the catalyst can be in any suitable form, but is more typically one or more rhenium-containing compounds (e.g., a rhenium oxide) or complexes.

Preferably, the catalyst comprises 100 to 3000 ppm by weight of rhenium, relative to the total weight of the catalyst. It is preferred that the catalyst comprises 250 to 2000 ppm by weight of rhenium, more preferably 500 to 1500 ppm by weight of rhenium, relative to the total weight of the catalyst.

In some embodiments, the catalyst may include a promoting amount of an alkali metal or a mixture of two or more alkali metals. Suitable alkali metal promoters include, for example, lithium, sodium, potassium, rubidium, cesium or combinations thereof. The amount of alkali metal, e.g. potassium, will typically range from 50 ppm to 5000 ppm, more typically from 300 ppm to 2500 ppm, most typically from 500 ppm to 1500 ppm expressed in terms of the alkali metal relative to the total weight of the catalyst. The amount of alkali metal is determined by the amount of alkali metal contributed by the refractory support and the amount of alkali metal contributed by the impregnation solution described below.

Combinations of heavy alkali metals like cesium (Cs) or rubidium (Rb) with light alkali metals like lithium (Li), sodium (Na) and potassium (K) are particularly preferred.

Cesium is an especially preferred alkali metal promoter. Preferably, the catalyst comprises 100 to 2000 ppm by weight of cesium, relative to the total weight of the catalyst. It is preferred that the catalyst comprises 400 to 1750 ppm by weight of cesium, more preferably 600 to 1500 ppm by weight of cesium, relative to the total weight of the catalyst.

Preferably the catalyst contains at least two light alkali metals, selected from sodium, potassium and lithium. Most preferably the catalyst contains sodium, potassium and lithium.

Preferably, the catalyst comprises 40 to 1170 ppm by weight of potassium, relative to the total weight of the catalyst. It is preferred that the catalyst comprises 100 to 1000 ppm by weight of potassium, most preferably 140 to 500 ppm by weight of potassium. The amount of potassium is determined by the amount of potassium contributed by the refractory support and the amount of potassium contributed by the impregnation solution described below.

Preferably, the catalyst comprises 100 to 2000 ppm by weight of lithium, relative to the total weight of the catalyst. It is preferred that the catalyst comprises 150 to 1500 ppm by weight of lithium, most preferably 300 to 1000 ppm by weight of lithium. The amount of lithium is determined by the amount of lithium contributed by the refractory support and the amount of lithium contributed by the impregnation solution described below.

Preferably, the catalyst comprises 10 to 1000 ppm by weight of sodium, relative to the total weight of the catalyst. It is preferred that the catalyst comprises 20 to 500 ppm by weight of sodium, most preferably 30 to 250 ppm by weight of sodium. The amount of sodium is determined by the amount of sodium contributed by the refractory support and the amount of sodium contributed by the impregnation solution described below.

The catalyst may also include a Group IIA alkaline earth metal or a mixture of two or more Group IIA alkaline earth metals. Suitable alkaline earth metal promoters include, for example, beryllium, magnesium, calcium, strontium, and barium or combinations thereof. The amounts of alkaline earth metal promoters can be used in amounts similar to those used for the alkali or transition metal promoters.

The catalyst may also include a promoting amount of a main group element or a mixture of two or more main group elements. Suitable main group elements include any of the elements in Groups IIIA (boron group) to VIIA (halogen group) of the Periodic Table of the Elements. For example, the catalyst can include a promoting amount of sulfur, phosphorus, boron, halogen (e.g., fluorine), gallium, or a combination thereof.

The catalyst may also include a promoting amount of a rare earth metal or a mixture of two or more rare earth metals. The rare earth metals include any of the elements having an atomic number of 57-103. Some examples of these elements include lanthanum (La), cerium (Ce), and samarium (Sm). The amount of rare earth metal promoters can be used in amounts similar to those used for the transition metal promoters.

To provide promoting species in the epoxidation catalyst, at least the second aqueous silver impregnation solution comprises one or more promoting species, in particular a transition metal promoter such as rhenium. It was found that the presence of high amounts of oxygen in the heating step is detrimental to the effectiveness of the above-described transition metal promoters, such as rhenium. Without wishing to be bound by theory, it is believed that at high temperatures transition metal promotors such as rhenium and tungsten increasingly form sites of reduced selectivity in the presence of oxygen. Thus, it is preferable that the first aqueous silver impregnation solution is free of transition metal promoters. In a preferred embodiment, the first aqueous silver impregnation solution and/or the second aqueous silver impregnation solution comprises one or more alkali metal promoters, in particular potassium Further provided is a silver-based epoxidation catalyst obtainable by a process according to any one of the embodiments described above. It is understood that all embodiments relating to the process of producing the epoxidation catalyst also apply to the epoxidation catalyst itself, where applicable.

Further provided is a process for producing an alkylene oxide by gas-phase oxidation of an alkylene, comprising reacting an alkylene and oxygen in the presence of a silver-based epoxidation catalyst as obtainable by a process according to any one of the embodiments described above. It is understood that all embodiments relating to the process of producing the epoxidation catalyst also apply to the process for producing ethylene oxide in the presence of the silver-based epoxidation catalyst, where applicable.

Suitable alkenes include ethylene, propylene, 1-butene, isobutene, 2-butene, 1,3-butadiene and 1,9-decadiene, or combinations thereof. Preferably, the process for producing an alkylene oxide by gas-phase oxidation of an alkylene is a process for producing ethylene oxide by gas-phase oxidation of ethylene.

The epoxidation can be carried out by all processes known to those skilled in the art. It is possible to use all reactors which can be used in the ethylene oxide production processes of the prior art; for example externally cooled shell-and-tube reactors (cf. Ullmann's Encyclopedia of Industrial Chemistry, 5th edition, vol. A-10, pp. 117-135, 123-125, VCH-Verlagsgesellschaft, Weinheim 1987) or reactors having a loose catalyst bed and cooling tubes, for example the reactors described in DE-A 3414717, EP 0082609 and EP-A 0339748.

The oxidation is preferably carried out in at least one tube reactor, preferably in a shell-and-tube reactor. On a commercial scale, ethylene epoxidation is preferably carried out in a multi-tube reactor that contains several thousand tubes. The catalyst is filled into the tubes, which are placed in a shell that is filled with a coolant. In commercial applications, the internal tube diameter is typically in the range of 20 to 40 mm (see, e.g., U.S. Pat. No. 4,921,681) or more than 40 mm (see, e.g., WO2006/102189).

To produce ethylene oxide from ethylene and oxygen, it is possible to carry out the reaction under conventional reaction conditions as described, for example, in DE-A 2521906, EP-A 0 014 457, DE-A 2300512, EP-A 0 172 565, DE-A 2454972, EP-A 0 357 293, EP-A 0 266 015, EP-A 0 085 237, EP-A 0 082 609 and EP-A 0 339 748. Inert gases such as nitrogen or gases which are inert under the reaction conditions, e.g. steam, methane, and also optionally reaction moderators, for example halogenated hydrocarbons such as ethyl chloride, vinyl chloride or 1,2-dichloroethane can additionally be mixed into the reaction gas comprising ethylene and molecular oxygen.

The oxygen content of the reaction gas is advantageously in a range in which no explosive gas mixtures are present. A suitable composition of the reaction gas for producing ethylene oxide can, for example, comprise an amount of ethylene in the range from 10 to 80% by volume, preferably from 20 to 60% by volume, more preferably from 25 to 50% by volume and particularly preferably in the range from 25 to 40% by volume, based on the total volume of the reaction gas. The oxygen content of the reaction gas is advantageously in the range of not more than 10% by volume, preferably not more than 9% by volume, more preferably not more than 8% by volume and very particularly preferably not more than 7.5% by volume, based on the total volume of the reaction gas.

The reaction gas preferably comprises a chlorine-comprising reaction moderator such as ethyl chloride, vinyl chloride or 1,2-dichloroethane in an amount of from 0 to 15 ppm by weight, preferably in an amount of from 0.1 to 8 ppm by weight, based on the total weight of the reaction gas. The remainder of the reaction gas generally comprises hydrocarbons such as methane and also inert gases such as nitrogen. In addition, other materials such as steam, carbon dioxide or noble gases can also be comprised in the reaction gas.

The concentration of carbon dioxide in the feed (i.e. the gas mixture fed to the reactor) typically depends on the catalyst selectivity and the efficiency of the carbon dioxide removal equipment. Carbon dioxide concentration in the feed is preferably at most 3 vol-%, more preferably less than 2 vol.-%, most preferably less than 1 vol.-%, relative to the total volume of the feed. An example of carbon dioxide removal equipment is provided in U.S. Pat. No. 6,452,027. The feed may be in the form of a circulating gas flow, and it is understood that the carbon dioxide concentrations apply to this circulating gas flow as well. Excess carbon dioxide may be removed from the circulating gas flow by, e.g., a carbon dioxide absorber.

The above-described constituents of the reaction mixture may optionally each have small amounts of impurities. Ethylene can, for example, be used in any degree of purity suitable for the gas-phase oxidation according to the invention. Suitable degrees of purity include, but are not limited to, "polymer-grade" ethylene, which typically has a purity of at least 99%, and "chemical-grade" ethylene which typically has a purity of less than 95%. The impurities typically comprise, in particular, ethane, propane and/or propene.

The reaction or oxidation of ethylene to ethylene oxide is usually carried out at elevated catalyst temperatures. Preference is given to catalyst temperatures in the range of $150$ to $350°$ C., more preferably $180$ to $300°$ C., particularly preferably $190$ to $280°$ C. and especially preferably $200$ to $280°$ C. The present invention therefore also provides a process as described above in which the oxidation is carried out at a catalyst temperature in the range $180$ to $300°$ C., preferably $200$ to $280°$ C. Catalyst temperature can be determined by thermocouples located inside the catalyst bed. As used herein, the catalyst temperature or the temperature of the catalyst bed is deemed to be the weight average temperature of the catalyst bodies.

The reaction according to the invention (oxidation) is preferably carried out at pressures in the range of 5 to 30 bar. All pressures herein are absolute pressures, unless noted otherwise. The oxidation is more preferably carried out at a pressure in the range of 5 to 25 bar, such as 10 bar to 20 bar and in particular 14 bar to 20 bar. The present invention therefore also provides a process as described above in which the oxidation is carried out at a pressure in the range of 14 bar to 20 bar.

The process for producing an alkylene oxide according to the invention is preferably carried out under conditions conducive to obtain a reaction mixture containing at least 2.0 vol.-% of ethylene oxide. In other words, the ethylene oxide outlet concentration (ethylene oxide concentration at the reactor outlet) is preferably at least 2.0 vol.-%. The ethylene oxide outlet concentration is more preferably in the range of 2.2 to 4.0 vol.-%, most preferably in the range of 2.9 to 3.5 vol.-%.

The oxidation is preferably carried out in a continuous process. If the reaction is carried out continuously, the GHSV (gas hourly space velocity) is, depending on the type of reactor chosen, for example on the size/cross-sectional area of the reactor, the shape and size of the catalyst, preferably in the range from 800 to 10,000/h, preferably in the range from 2,000 to 8,000/h, more preferably in the range from 2,500 to 6,000/h, most preferably in the range from 4,500 to 5,500/h, where the values indicated are based on the volume of the catalyst.

In one embodiment, the EO-space-time-yield measured is greater than $180$ $kg_{EO}/(m^3_{cat}h)$, preferably to an EO-space-time-yield of greater than $200$ $kg_{EO}/(m^3_{cat}h)$, such as greater than $250$ $kg_{EO}/(m^3_{cat}h)$, greater than $280$ $kg_{EO}/(m^3_{cat}h)$, or greater than $300$ $kg_{EO}/(m^3_{cat}h)$. Preferably the EO-space-time-yield measured is less than $500$ $kg_{EO}/(m^3_{cat}h)$, more preferably the EO-space-time-yield is less than $350$ $kg_{EO}/(m^3_{cat}h)$.

The production of ethylene oxide from ethylene and oxygen can advantageously be carried out in a recycle process. After each pass, the newly formed ethylene oxide and the by-products formed in the reaction are removed from the product gas stream. The remaining gas stream is supplemented with the required amounts of ethylene, oxygen and reaction moderators and reintroduced into the reactor. The separation of the ethylene oxide from the product gas stream and its work-up can be carried out by customary methods of the prior art (cf. Ullmann's Encyclopedia of Industrial Chemistry, 5th edition, vol. A-10, pp. 117-135, 123-125, VCH-Verlagsgesellschaft, Weinheim 1987).

The invention will be described in more detail by the subsequent examples.

Method 1—Analysis of Silver Content

Shaped catalyst bodies were crushed and pulverized so as to obtain homogenized samples. 300 to 700 mg of pulverized catalyst bodies were weighed into a titrator (888 Titrando, Metrohm). The sample was brought into contact with 10 mL of a mixture of 65% $HNO_3$:$H_2O$ (1:1) at boiling temperature. The obtained mixture was diluted with 150 mL of $H_2O$ and titrated with a 0.1 M solution of ammonium thiocyanate, using a silver electrode.

Method 2—Side Crush Strength

The side crush strength was determined using an apparatus of the "Z 2.5/T 919" type supplied by Zwick Röll (Ulm), stamp size: 12.7 mm×12.7 mm. Based on measurements of 25 randomly selected shaped bodies, average values were calculated. The measurements were performed along two directions—along the side and along the diagonal. In the measurement along the diagonal, the force is exerted along an axis running through a first outer passageway, the central passageway and a second outer passageway opposite to the first outer passageway. In the measurement along the side, the force is exerted along two axes each running through a two outer passageways.

Method 3—Attrition Loss

Attrition loss was determined according to ASTM D4058-96.

Refractory Support

The refractory support A used in Example 1 was an alumina support and comprised Si, Ca, Mg, Na, K and Fe as chemical impurities. Support A was obtained from EXACER s.r.l. (Via Puglia 2/4, 41049 Sassuolo (MO), Italy), under the lot number COM 32/19.

Support A had $Si_{Al2O3}=500$ ppm, $Ca_{Al2O3}=400$ ppm, $Mg_{Al2O3}=200$ ppm, $Na_{Al2O3}=95$ ppm, $K_{Al2O3}=170$ ppm, $Fe_{Al2O3}=100$ ppm. Support A had a total pore volume of 0.55 mL/g and a bimodal pore size distribution with the first log differential pore volume distribution peak in the range of 0.4 to 0.6 μm and the second log differential pore volume distribution peak in the range of 10 to 30 μm as measured by Hg intrusion according to DIN 66133. Furthermore, support A had a BET surface area of 1.93 $m^2/g$. The support had a tetralobe shape with five passageways. The support exhibited a side crush strength of 96 N measured along the side and an attrition loss of 20 wt.-%.

EXAMPLES

Example 1—Preparing Shaped Catalyst Bodies

Shaped catalyst bodies according to Table 1 below were prepared by impregnating support A with a silver impregnation solution. The catalyst composition is shown in Table 1 below.

TABLE 1

Catalyst composition (Ag-contents are reported in percent by weight of total catalyst, dopant values are reported in parts per million by weight of total catalyst)

| $Ag_{CAT}$ * [wt.-%] | $Li_{CAT}$ [ppm] | $S_{CAT}$ [ppm] | $W_{CAT}$ [ppm] | $Cs_{CAT}$ [ppm] | $Re_{CAT}$ [ppm] | $K_{ADD}$ ** [ppm] | $K_{CAT}$ *** [ppm] |
|---|---|---|---|---|---|---|---|
| 28.9 | 470 | 35 | 570 | 950 | 1200 | 93 | 213 |

* Ag and all promoter values are calculated values;
** $K_{ADD}$ is understood to mean the amount of potassium added during impregnation and does not include the amount of potassium comprised in the alumina support prior to impregnation;
*** $K_{CAT}$ is understood to mean the total amount of potassium in the catalyst

1.1 Production of the Silver Complex Solution

Silver complex solution was prepared according to Production Example 1 of WO 2019/154863 A1. The silver complex solution had a density of 1.529 g/mL, a silver content of 29.3 wt.-% and a potassium content of 90 ppm.

1.2. Preparation of Intermediate Catalysts 315.2 g of support A were placed into a 2 L glass flask. The flask was attached to a rotary evaporator, which was set under a vacuum pressure of 80 mbar. The rotary evaporator system was set in rotation of 30 rpm. 251.7 g of silver complex solution prepared according to step 1.1 were added onto support A over 15 min under a vacuum pressure of 80 mbar. After addition of the silver complex solution, the rotary evaporator system was continued to rotate under vacuum for a further 15 min. The impregnated support was then left in the apparatus at room temperature (approximately 25° C.) and atmospheric pressure for 1 h and mixed gently every 15 min.

The impregnated material was placed on a net forming 1 to 2 layers (about 100 to 200 g per heating run). The net was subjected either to 23 Nm$^3$/h nitrogen flow (oxygen content: <20 ppm) (intermediates 1.1, 1.3) or 23 Nm$^3$/h of air flow (intermediates 1.2, 1.4), wherein the gas flows were preheated to a temperature of 305° C. The impregnated materials were heated up to a temperature of 290° C. at a heating rate of about 30 K/min and then maintained at 290° C. for 8 min to yield Ag-containing intermediate products according to Table 2. The temperatures were measured by placing three thermocouples at 1 mm below the net. Subsequently, the catalysts were cooled to ambient temperature by removing the intermediate catalyst bodies from the net using an industrial vacuum cleaner.

TABLE 2

Ag containing intermediate catalysts (Ag-contents are reported in percent by weight of total catalyst, dopant values are reported in parts per million by weight of total intermediate catalyst)

| Intermediate | Support | $Ag_{CAT}$ * [wt.-%] | $K_{ADD}$ ** [ppm] | $K_{INT}$ *** [ppm] | Heating Inlet Gas |
|---|---|---|---|---|---|
| 1.1 | A | 19.0 | 58 | 138 | Nitrogen |
| 1.2 | A | 19.0 | 58 | 138 | Air |
| 1.3 | A | 19.0 | 58 | 138 | Nitrogen |
| 1.4 | A | 19.0 | 58 | 138 | Air |

* Ag and all promoter values are calculated values;
** $K_{ADD}$ is understood to mean the amount of potassium added during impregnation and does not include the amount of potassium comprised in the alumina support prior to impregnation;
*** $K_{INT}$ is understood to mean the total amount of potassium in the intermediate 1.3. Preparation of Catalysts 170.7 g of Ag-containing intermediate products 1.1 to 1.4 as prepared according to step 1.2 were each placed into a 2 L glass flask. The flask was attached to a rotary evaporator which was set under vacuum pressure of 80 mbar. The rotary evaporator system was set in rotation of 30 rpm. 82.09 g of the silver complex solution prepared according to step 1.1 was mixed with 3.22 g of promoter solution I, 3.71 g of promoter solution II, and 6.34 g of promoter solution III.

Promoter solution I was obtained by dissolving lithium nitrate (FMC, 99.3%) and ammonium sulfate (Merck, 99.4%) in DI water to achieve a Li content of 2.85 wt.-% and a S content of 0.21 wt.-%. Promoter solution II was obtained by dissolving tungstic acid (HC Starck, 99.99%) in DI water and cesium hydroxide in water (HC Starck, 50.42%) to achieve a target Cs content of 5.0 wt.-% and a W content of 3.0 wt.-%. Promoter solution III was obtained by dissolving ammonium perrhenate (Engelhard, 99.4%) in DI water to achieve a Re content of 3.7 wt.-%.

The combined impregnation solution containing silver complex solution and promoter solutions I, II, and III was stirred for 5 minutes. The combined impregnation solution was added onto each of the silver-containing intermediate products 1.1 to 1.4 over 15 min under a vacuum pressure of 80 mbar. After addition of the combined impregnation solution, the rotary evaporator system was continued to rotate under vacuum for another 15 min. The impregnated support was then left in the apparatus at room temperature (about 25° C.) and atmospheric pressure for 1 h and mixed gently every 15 min.

The impregnated material was placed on a net forming 1 to 2 layers (about 100 to 250 g per heating run). The net was subjected either to 23 Nm$^3$/h nitrogen flow (oxygen content: <20 ppm) (catalysts C1.1, C1.2) or 23 Nm$^3$/h of air flow (catalysts C1.3, C1.4), wherein the gas flows were preheated to a temperature of 305° C. The impregnated materials were heated up to a temperature of 290° C. at a heating rate of about 30 K/min and then maintained at 290° C. for 7 min to yield Ag-containing intermediate products according to Table 1. The temperatures were measured by placing three thermocouples at 1 mm below the net. Subsequently, the catalysts were cooled to ambient temperature by removing the catalyst bodies from the net using an industrial vacuum cleaner.

Example 2—Catalyst Testing

An epoxidation reaction was conducted in a vertically-placed test reactor constructed from stainless steel with an inner diameter of 6 mm and a length of 2.2 m. The reactor was heated using hot oil contained in a heating mantel at a specified temperature. All temperatures below refer to the temperature of the hot oil. The reactor was heated to a temperature of 90° C. under nitrogen. The reactor was then charged with 9 g of inert steatite balls (0.8 to 1.1 mm), onto which 26.4 g of crushed catalyst screened to a desired particle size of 1.0 to 1.6 mm were packed, and thereon an additional 29 g of inert steatite balls (0.8 to 1.1 mm) were packed. An inlet gas was introduced to the top of the reactor in a "once-through" operation mode. The inlet gas was a nitrogen flow of 130 NL/h, at a pressure of 1.5 bar absolute and a temperature of 90° C. The reactor temperature was ramped up to 210° C. at a heating rate of 50 K/h, and the catalysts were maintained under these conditions for 15 h.

Subsequently, the nitrogen flow was changed to a flow of 114 NL/h methane and 1.5 NL/h $CO_2$. The reactor was pressurized to 16 bar absolute. Then, 30.4 NL/h ethylene and 0.8 NL/h of a mixture of 500 ppm ethylene chloride in methane were added. Subsequently, oxygen was introduced in a stepwise manner to reach a final flow of 6.1 NL/h. At this point, the inlet composition consisted of 20 vol.-% ethylene, 4 vol.-% oxygen, 1 vol.-% carbon dioxide, and ethylene chloride (EC) moderation of 2.5 parts per million by volume (ppmv), with methane used as a balance at the total gas flow rate of 152.8 NL/h.

The reactor temperature was ramped up to 225° C. at a heating rate of 5 K/h and afterwards to 240° C. at a heating rate of 2.5 K/h. The catalysts were maintained at this condition for 135 h. Afterwards, EC concentration was decreased to 2.0 ppmv, and the temperature was decreased to 225° C. Then, the inlet gas composition was gradually changed to 35 vol.-% ethylene, 7 vol.-% oxygen, 1 vol.-% carbon dioxide with methane used as a balance and a total gas flow rate of 147.9 NL/h. The temperature was adjusted to achieve an ethylene oxide (EO) concentration in the outlet gas of 3.05%. The EC concentration was adjusted to optimize the selectivity. Results of the catalyst tests are summarized in Table 3.

TABLE 3

| | C1.1 Comparative | C1.2 Inventive | C1.3 Comparative | C1.4 Comparative |
|---|---|---|---|---|
| Catalyst | | | | |
| Heating inlet gas after $1^{st}$ impregnation | Nitrogen | Air | Nitrogen | Air |
| Heating inlet gas after $2^{nd}$ impregnation | Nitrogen | Nitrogen | Air | Air |

| Time-on-stream [h] | Performance | | | |
|---|---|---|---|---|
| 600 | Catalyst temperature [° C.] | 232 | 233 | 234 | 234 |
| | Selectivity [%] | 89.3 | 89.5 | 88.6 | 88.4 |

It is evident that catalyst C1.2, which was obtained by a first heating step under air and a second heating step under nitrogen, displays a selectivity equivalent to or even better than that of catalyst C1.1, which was obtained by two heating steps under nitrogen. Catalyst C1.2 also has a higher selectivity than catalyst C1.3, which was obtained by a first heating step under nitrogen and a second heating step air, and catalyst C1.4, which was obtained by two heating steps under air.

The invention claimed is:

1. A process for producing a silver-based epoxidation catalyst, comprising i) impregnating a particulate porous refractory support comprising at least 90 wt % alpha-alumina with a first aqueous silver impregnation solution comprising silver ions and an aminic complexing agent selected from amines, alkanolamines and amino acids;

ii) converting at least part of the silver ions impregnated on the refractory support to metallic silver by heating while directing a stream of a first gas over the impregnated refractory support to obtain an intermediate catalyst, wherein the first gas comprises at least 5 vol.-% oxygen;

iii) impregnating the intermediate catalyst with a second aqueous silver impregnation solution comprising silver ions, an aminic complexing agent selected from amines, alkanolamines and amino acids, and one or more transition metal promoters; and iv) converting at least part of the silver ions impregnated on the intermediate catalyst to metallic silver by heating while directing a stream of a second gas over the impregnated intermediate catalyst to obtain the epoxidation catalyst, wherein the second gas comprises at most 2.0 vol.-% oxygen;

wherein the impregnated refractory support and the impregnated intermediate catalyst are each heated to a temperature of 200 to 800° CU;

wherein the aminic complexing agent in the first and second impregnation solution comprises a vicinal $C_2$-$C_6$-alkylenediamine.

2. The process according to claim 1, additionally comprising ii') subsequent to ii) and prior to iii), cooling the intermediate catalyst; and/or iv') subsequent to iv), cooling the catalyst.

3. The process according to claim 2, wherein in step iv') the catalyst is cooled while directing a stream of the second gas over the impregnated intermediate catalyst to obtain the epoxidation catalyst until the temperature of the catalyst is 100° C. or lower.

4. The process according to claim 1, wherein the first gas comprises at least 10 vol.-% oxygen.

5. The process according to claim 4, wherein the first gas is air.

6. The process according to claim 1, wherein the second gas comprises at least 98 vol.-% nitrogen.

7. The process according to claim 1, wherein the first aqueous silver impregnation solution and/or the second aqueous silver impregnation solution comprise a carboxylate anion.

8. The process according to claim 1, wherein the first aqueous silver impregnation solution is free of transition metal promoters.

9. The process according to claim 1, wherein the first aqueous silver impregnation solution and/or the second aqueous silver impregnation solution comprises one or more alkali metal promoters.

10. The process according to claim 1, wherein the impregnated refractory support and the impregnated intermediate catalyst are each heated to a temperature of 210 to 650° C.

11. The process according to claim 1, wherein the heating rate in the temperature range of 40 to 200° C. is at least 20 K/min.

12. The process according to claim 1, wherein the impregnated refractory support and the impregnated intermediate catalyst are each heated for a total period of 5 to 60 min.

13. The process according to claim 1, wherein the impregnated refractory support and the impregnated intermediate catalyst are each heated at an absolute pressure in the range of 0.9 to 1.1 bar.

14. The process according to claim 1, wherein the intermediate catalyst is impregnated with the second aqueous silver impregnation solution in step iii) sufficient so as to obtain an epoxidation catalyst comprising 15 to 50 wt.-% silver, relative to the total weight of the catalyst.

15. A silver-based epoxidation catalyst obtained by the process according to claim 1.

16. A process for producing an alkylene oxide by gas-phase oxidation of an alkylene, comprising reacting an alkylene and oxygen in the presence of a silver-based epoxidation catalyst obtained by the process according to claim 1.

17. The process according to claim 1, wherein the second aqueous silver impregnation solution comprises silver ions, an aminic complexing agent selected from amines, alkanolamines and amino acids, and rhenium.

* * * * *